(12) United States Patent
Lenig

(10) Patent No.: US 9,867,738 B2
(45) Date of Patent: Jan. 16, 2018

(54) EAR WAX REMOVER AND CLEANER

(71) Applicant: John J. Lenig, Annandale, NJ (US)

(72) Inventor: John J. Lenig, Annandale, NJ (US)

( * ) Notice: Subject to any disclaimer, the term of this patent is extended or adjusted under 35 U.S.C. 154(b) by 68 days.

(21) Appl. No.: 15/149,335

(22) Filed: May 9, 2016

(65) Prior Publication Data

US 2017/0319391 A1    Nov. 9, 2017

(51) Int. Cl.
*A61F 9/00*      (2006.01)
*A61F 11/00*    (2006.01)

(52) U.S. Cl.
CPC .................................. *A61F 11/006* (2013.01)

(58) Field of Classification Search
CPC ........ A61F 11/00; A61F 11/006; A61F 13/38; B08B 9/02; B08B 9/027; B08B 9/04
See application file for complete search history.

(56) References Cited

U.S. PATENT DOCUMENTS

| | | | |
|---|---|---|---|
| 5,715,559 A * | 2/1998 | Mitri | A61F 13/38 15/118 |
| 5,715,850 A | 2/1998 | Markgraaf et al. | |
| 5,888,199 A | 3/1999 | Karell et al. | |
| 5,899,568 A | 4/1999 | Vanraes et al. | |
| 6,033,417 A | 3/2000 | Tseng et al. | |
| 6,270,510 B1 * | 8/2001 | Westendorf | A61B 17/24 606/162 |
| 6,699,331 B1 | 3/2004 | Kritzler et al. | |
| 7,074,230 B2 | 7/2006 | Olson et al. | |
| 7,658,745 B2 | 2/2010 | Olson et al. | |
| 8,096,306 B2 | 1/2012 | Malvar | |
| 8,197,403 B2 | 5/2012 | Johnson et al. | |
| 8,783,787 B2 | 7/2014 | Basari et al. | |
| 8,850,650 B2 | 10/2014 | Basari et al. | |
| 2001/0001828 A1 | 5/2001 | Begun et al. | |
| 2005/0133056 A1 | 1/2005 | Beguin et al. | |
| 2005/0081874 A1 | 4/2005 | Mathiez | |
| 2006/0085018 A1 * | 4/2006 | Clevenger | A61F 11/006 606/162 |
| 2008/0313838 A1 * | 12/2008 | Nakatani | A61F 11/006 15/236.01 |
| 2010/0319720 A1 | 3/2010 | Thorne et al. | |
| 2011/0092889 A1 * | 4/2011 | Daniels | A61M 35/00 604/22 |
| 2012/0283616 A1 * | 11/2012 | Edme | A61F 13/38 604/1 |
| 2015/0005793 A1 * | 1/2015 | Collins | A61F 11/006 606/162 |
| 2016/0310154 A1 * | 10/2016 | Harkless | A61B 17/24 |

* cited by examiner

*Primary Examiner* — Jonathan Miles
(74) *Attorney, Agent, or Firm* — Craig M. Bell

(57) ABSTRACT

The present invention comprises a disposable ear brush which is an ear cleaning device comprising a one piece, flexible wire shaft that forms two twisted wire shaft arms with a plurality of soft, angled bristles disposed at each end. The twisted wire shaft and bristles may be safely inserted into the ear canal and subsequently withdrawn pulling the bristles and any collected earwax therein from the ear canal.

8 Claims, 1 Drawing Sheet

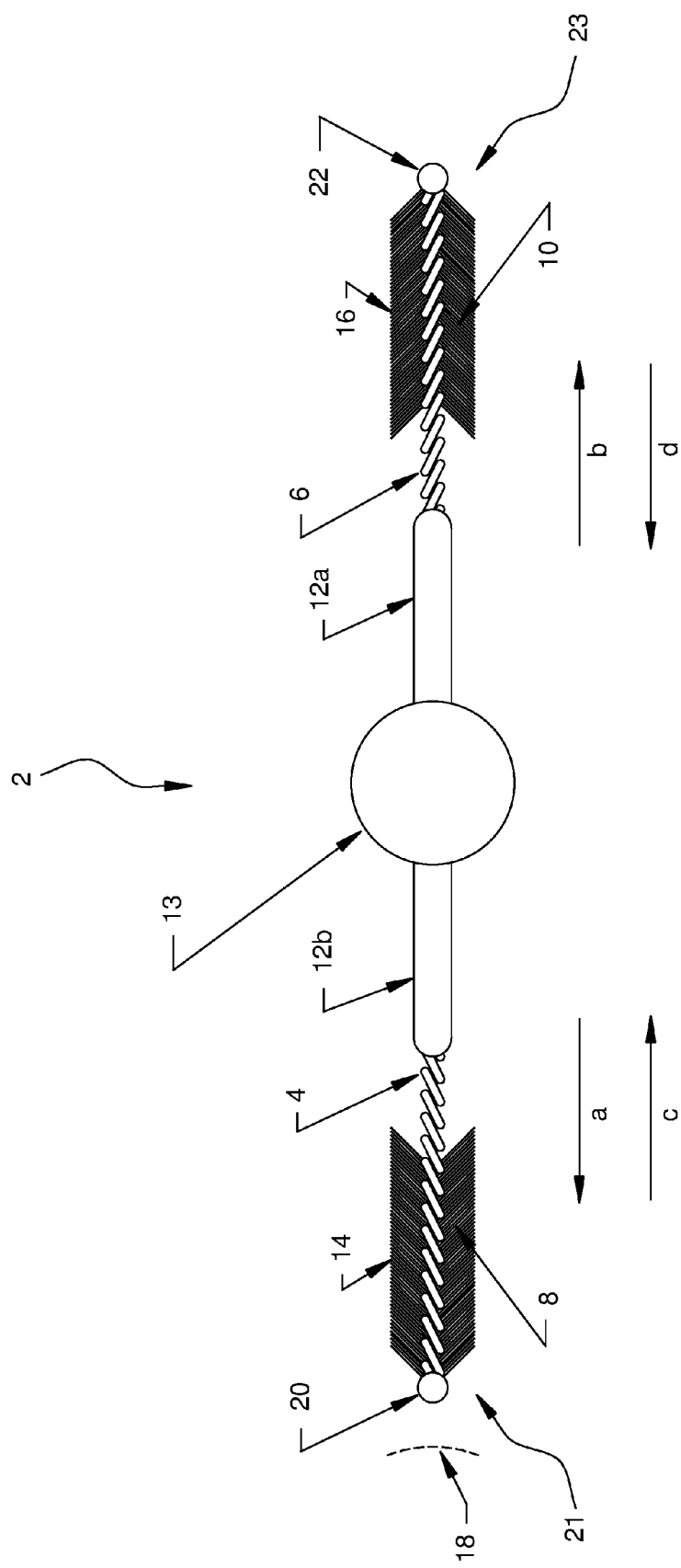

EAR WAX REMOVER AND CLEANER

FIELD OF THE INVENTION

The present invention relates generally to consumer health care medical devices useful in the cleaning and caring of the human ear canal and methods for their use. More specifically, the present invention relates to an ear canal cleaning device that safely and effectively removes ear wax and cerumen for better auditory health and hearing.

BACKGROUND OF THE INVENTION

The human ear canal is essentially divided into two parts. An elastic cartilage section forms the outer third of the canal, it's anterior and lower wall are cartilaginous, whereas the inner and back wall are fibrous. The cartilage comprises a cartilage framework known as the pinna. The bony part forms the inner two thirds. The bony part is much shorter in children and is only a ring known as the annulus tympanicus. The size and shape of the ear canal varies among individuals and is approximately 2.5 centimeters (1 in) long and 0.7 centimeters (0.28 in) in diameter in most people. It has a circular or sigmoidol form and runs from behind the aural opening and then downward and forward. Cross-sectionally, it possesses an oval shape.

Ear wax, (cerumen) is a yellowish, waxy substance secreted in the ear canals. It plays an important role in humans as it assists in cleaning detritus from inside the ear while its' residue provides a lubrication function and provides some protection from bacteria, fungi, and insects. The presence of a surface coating or residue of wax on the surface of the ear canal is necessary to continue protecting the sensitive middle ear from insects, dirt and microbial infection. Whereas the accumulation of too much ear wax over time due to its' continual secretion by the glands discussed above is detrimental to ones' hearing, cleaning the canal by washing out the ear wax with a solution is uncomfortable and can actually remove too much wax leaving the middle ear vulnerable to the dangerous elements (dirt, microbes, etc.) discussed earlier.

Nevertheless, the continual excretion of cerumen without its' removal somehow can result in an accumulation thereof and if the more liquid form of cereum hardens and becomes excess or impacted the cerumen wax build-up can press against the eardrum and/or occlude the external auditory canal and impair hearing, causing conductive hearing loss. One of the beneficial aspects of ear wax, produced by the glands in the ear canal can oftentimes accumulate and will trap dust and other small dirt particles and prevent them from reaching, and potentially damaging or infecting the eardrum. Normally, the wax dries up and falls out of the ear, along with any trapped dust or debris. Everyone makes ear wax, but the amount and type are genetically determined just like hair color or height. Smaller or oddly shaped ear canals may make it difficult for the naturally occurring wax to get out of the canal and lead to wax impactions.

Blockage of the ear canal, also known as ear impaction, also occurs when the wax gets pushed deep within the ear canal. Ear wax blockage affects about 6% of people and is one of the most common ear problems doctors encounter The most common cause of impactions is the use of Q-tips (and other objects such as bobby pins and rolled napkin corners), which can remove some superficial wax on the outer ear canal but this may also push the rest of the wax deeper into the ear canal. Hearing aid and earplug users are also more prone to ear wax blockage. Symptoms of an ear wax impaction include decreased hearing, dizziness, ear pain, a plugged up head or fullness sensation, and tinnitus or ringing in the ear.

Over-the-counter wax softening drops such as Debrox® or Murine® may be used to clean the outer ear, but these again must be put into put into an affected ear, and then allowed to drain out after about five minutes while holding the head to the side, allowing the drops to settle. A bulb-type syringe may be used to gently flush the ear with warm water. There are several methods of removing excess cerumen. A common method is to syringe the ear canal with warm water and then flushing the cerumen out with the water. Various solutions of oils, peroxide, glycerine or detergents are also used to flush the ear canal. Cotton swabs are also commonly used, but not recommended as they generally only remove a small amount of wax and push the rest further into the ear canal.

Physically picking or scraping the ear wax out with an ear pick or curette is yet another method of removing ear wax usually performed by a health professional under direct observation with magnification. A less common method is ear candling which is the practice of lighting a specially made hollow ear candle and placing the unlit end in the patient's ear. It is claimed to create a slight vacuum that draws out debris and wax. There are some complications or risks associated with these various types of ear wax removal such as damage to the ear drum from excess pressure or physically perforating the ear drum.

A key limitation in the removal of ear wax or cerumen is the inability to directly observe the ear canal. A device called an otoscope provides a way to see into the ear canal. The otoscope has a handle and a head with a light source and a magnifying lens with a removable ear speculum that attaches to the front. The speculum is inserted into the external ear canal allowing the physician or examiner to look through the lens into the ear canal. Many models have a detachable sliding rear window allowing instruments to be inserted through the speculum into the ear canal that could be used for removing ear wax. The otoscope can only be used to observe the ear canal before or after flushing, but not during actual ear wax removal as a result the physician must repeatedly stop flushing to observe the progress being made.

U.S. Pat. No. 5,374,276 to Lay discloses the use of a cotton swab for cleaning the auditory canal and the cotton swab is removed and discarded from the ear cleaning device which is intended to be reused. The consumer is expected to wrap and secure a cotton swab around the spiral hatch pattern on the one end of the handle portion of the ear wax remover. An extraction head on this ear wax remover comprises three similarly shaped projections extending radially outward from a shank. Each projection has the shape of a frustum of a cone. That is, the extraction head comprises three frustum cone shapes portions on the tip of the device. Thus, the ear wax remover tool is to be used over and over again with subsequent swab attachments after each usage.

U.S. Pat. No. 7,074,230 to Olson discloses a disposable ear cleaning device comprising: one piece plastic body; a handle on the plastic body to be grasped and to be rotated; an integral scoop for removing ear wax on the plastic body at one end of the handle; the scoop having a bowl portion; upper edges on the bowl portion for scraping and collecting wax and for depositing the wax within the bowl portion; an outer smooth lower bowl surface on the bowl and a hollow interior in the bowl portion for collecting the wax in the bowl portion and for carrying ear wax deposited therein from the ear; an upper front outer edge of the bowl being at a lower height than an upper rear edge of the bowl; and a swab of bulbous shape at the other end of the handle for additional cleaning of the ear. The flexible neck portion is provided between the handle and the scoop to bend during use of the device and a cotton swab on an end of the handle opposite the bowl portion.

U.S. Pat. No. 7,658,745 also to Olson teaches a similar disposable ear cleaning device having a one-piece, plastic body with an integral scoop at one end having a bowl portion having a smooth lower surface on the bowl. Openings may be formed in the bottom of the bowl for scraping wax and debris from the ear. The preferred openings are parallel slots. The preferred bowl has rounded, upper edges at the rim for scraping ear wax with the front, distal end at a lower height than a rear end of the bowl which is joined to a handle. The preferred handle may be fluted for gripping and turning the bowl when scraping ear wax. A flexible neck may join the bowl to the handle. A bulbous end of plastic or of cotton may be provided at the end of the device opposite the bowl. The referred cleaning device weighs less than one gram and is inexpensive.

BRIEF DESCRIPTION OF THE DRAWINGS

FIG. 1 is a side view of the disposable ear brush cleaning and removal device of the present invention.

SUMMARY OF THE INVENTION

The present invention comprises a disposable ear brush which is an ear cleaning device comprising a one piece, flexible wire shaft that forms two twisted wire shaft arms with a plurality of soft, angled bristles disposed at each end. The twisted wire shaft and bristles may be safely inserted into the ear canal and subsequently withdrawn pulling the bristles and any collected earwax therein from the ear canal.

DETAILED DESCRIPTION OF THE INVENTION

It is an object of the present invention to provide a device and a method for its' use to safely and effectively clean the human ear of cerebrum and dried ear wax with any accumulated detritus therein. It is a further object of the present invention to provide a device and a method for its' use to clean the human ear that stimulates the auditory nerves along the lining of the ear so as to effect a pleasant feeling to the user while providing a safety element that prevents damage to the inner ear and ear canal.

Referring now to FIG. 1, the disposable ear brush of the present invention comprises an ear cleaning device consisting of an elongated body 2 comprising a pair of twisted wire arms 4 and 6 with a first proximal end 8 and a second distal end 10 with a centrally disposed, substantially spheroidal, connector 12 which also serves as a handle there between. The central connector element 12 which forms a handle for the device between the twisted wire arms 4 and 6 can be grasped and the device held between the thumb and forefinger in this manner. Whereas each side of the cleaner may be used at a time, arm 21 may be inserted into one ear at one time and arm 23 into the other ear later. The handle 12 has a centrally enlarged, rounded spheroidal center 13 with a circumference considerably larger than either of the wire arms 4, 6 and the handle elements 12a, 12b and this may be slowly and gently pressed up against the users' ear canal in the direction of arrow a from one side and (or arrow d from the other) swiveled or rotated in a 360° manner about the central axis of the device thereby cleaning the ear canal lining of any cerumen, ear wax or dirt contained thereon. Emanating from the twisted wire arms 4, 6 along a substantial portion of their length are the cleaner bristles 14, 16 which are oriented at approximately a 45° angle rear-ward from the point of the devices' insertion into the ear. The angled orientation of the bristles 14, 16 allows for insertion of the arms of the device into the ear canal in the direction of arrows a or b without pushing wax and cerumen deeper therein and will grab onto and hold excessive wax when the device is pulled out of the ear for removal and cleaning (arrows c & d).

The soft, pliable bristles consist of preferably of a soft polymer plastic, and each group 14, 16 are angled back towards the central handle 12 of the device as shown. Again, the circumference formed by the outer peripheral tips of the bristles is smaller than that of the centrally located handle 12 which limits the depth of insertion of the device into the ear canal and prevents any damage or scarring. The tips of each twisted wire arm are rounded 20, 22 to prevent ear canal irritation during insertion of the device. In this way, when the device is inserted into the ear canal of the user and gently pressed inwardly in the direction of the ear drum 18, the pliable bristles 14, 16, upon pressing against the inner surface of the ear canal, bend back. The resilient nature and soft flexibility of the bristles makes them resistant to the force bending them back and adds some resistance to the bend-back so as to retain the bristles original position prior insertion into the ear canal. Therefore at a pre-determined point, i.e., when the centrally located handle 12 presses up against the outer ear canal, the user may pull back on the handle 12a of the shaft of the device in the direction of arrow c and the pliable bristles will scrape any ear wax, dirt, detritus and/or cerumen that is deposited on the surface of the ear canal. Due to the unique angled nature of the bristles, these can scrape off the wax from the surface of the ear canal and then retain said wax between them at the base thereof. Once removed from the ear canal, the ear cleaner device may be either thrown away or the bristles cleaned and re-used another time.

Referring now again to FIG. 1, the ear cleaner device of the present invention 2 comprises the twisted wire arms (4, 6) and bristles (8, 10) emanating there from. This then, is similar to a small brush. The outer tips (14, 16) of the bristles (8) define a roughly cylindrical shape of predetermined diameter, or a conical shape when viewed down along the central axis of the device from the tip of the proximal end towards the distal end. The size or length of the bristles may be further modified so as to arrive at various additional lengths and shapes so long as they are angled and oriented in a rear-wardly positioned manner at angle ($\alpha$) of from about 30° to about 45°. In this position, the shaft of the device may be slowly inserted into the ear canal from the external or outer ear inwardly toward the inner ear (see arrow a) and, due to the angle and pliability of the bristles will pass easily and encounter little resistance from the ear canal surface.

The disposable ear brush of the present invention promotes more frequent cleaning of the ears and the ear canals due to the inherent features which effectively clean the ears and comfortably remove the excess wax from deep inside the ear canal while leaving a surface coating of wax behind to continue protecting the middle ear from insects, dirt and microbial infection. The methods and devices used in the prior art such as washing out the ear wax with a solution is uncomfortable and can actually remove too much wax leaving the middle ear vulnerable to dangerous elements such as dirt and micro-organisms which the wax or cerumen is there in the first place to protect against. Currently available ear cleaners such as liquid solutions, pressure washers or vacuum systems are not intended to be used inside the ear canal and are for the outer ear areas only. Cotton swabs tend to push wax deeper into the ear and are not effective for a thoroughly clean ear canal.

In summary then, the present invention comprises disposable ear brush and cleaner comprising an elongate body consisting of at least two twisted wire arms connected by a substantially spheroidal handle. Each of the twisted wire arms has at least one set of flexible bristles located at the distal ends of said arms with at least one rounded tip located at opposite ends of each arm. Each bristle of each respective set of bristles is angled in parallel away from the distal ends of the arms and the auditory ear canal opening for easy insertion of the arms into the users ear canal. The spheroidal center or handle which joins the twisted wire arms at their anterior ends is larger than the opening of the outer ear so as to prevent the rounded tips of the device from contacting the eardrum 18.

The present invention also comprises a method for the removal of ear wax, cerebrum and other debris from the ear canal of a mammal using the ear brush cleaner described herein above. One or the other distal end of the brush cleaner is gently inserted into the ear canal of the user until the centrally disposed, substantially spherical handle, which is larger than the opening of the outer ear, gently contacts said outer ear opening. The handle is then gently rotated in a clockwise and counter-clockwise motion so that the bristles gently remove the ear wax, cerumen, dirt and detritus from the sides of the ear canal. The wire brushes of the ear brush cleaner are then withdrawn from the ear canal after handle rotation.

It is recognized that changes may be made to the specific elements and/or components of the device and the parameters and ranges disclosed herein and that there are a number of different ways known in the art to change the disclosed variables. And whereas it is understood that only the preferred embodiments of these elements are disclosed herein as set forth in the specification and drawings, the invention should not be so limited and should be construed in terms of the spirit and scope of the claims that follow herein.

What I claim is:

1. A disposable ear brush comprising:
    a) an elongate body comprising a plurality of twisted wire arms comprising a proximal end, a distal end, and a distal tip, the arms connected by a substantially spheroidal handle at the proximal end of each arm;
    b) at least one set of flexible bristles located at the distal end of each arm, wherein each bristle is angled away from the distal tip of each arm; and
    c) at least one rounded tip located at the distal tip of each arm.

2. The ear brush of claim 1 wherein each arm is comprised of a twisted pair of flexible wires.

3. The ear brush of claim 2 wherein said twisted pair of wires are joined at the proximal ends by a substantially spherical handle.

4. The ear brush of claim 3 wherein the substantially spherical handle is larger than the opening of the outer ear so as to prevent the rounded tips from contacting the eardrum.

5. A method for removal of ear wax, cerebrum and other debris from the ear canal of a mammal using the ear brush of claim 4.

6. The method of claim 5 wherein the distal end of one of the arms is gently inserted into the ear canal of the user until the substantially spherical handle gently contacts said outer ear opening.

7. The method of claim 6 wherein the substantially spherical handle is gently rotated in a clockwise motion and a counter-clockwise motion so that the bristles gently remove the ear wax, cerumen, dirt and detritus from the sides of the ear canal.

8. The method of claim 7 further comprising withdrawal of said arms from the ear canal after rotation of the handle.

\* \* \* \* \*